United States Patent [19]
Bruce

[11] Patent Number: 5,090,257
[45] Date of Patent: Feb. 25, 1992

[54] AUTOMATIC ISOKINETIC AEROSOL SAMPLING SYSTEM

[75] Inventor: Charles W. Bruce, Las Cruces, N. Mex.

[73] Assignee: The United States of America as represented by the Secretary of the Army, Washington, D.C.

[21] Appl. No.: 520,925

[22] Filed: May 9, 1990

[51] Int. Cl.$^5$ .............................................. G01N 1/24
[52] U.S. Cl. ............................. 73/863.03; 73/863.23; 73/864.34
[58] Field of Search ........... 73/863.02, 863.03, 863.23, 73/863.24, 863.25, 864.34, 864.35, 863.57, 863.58, 864.73, 864.74, 31.07

[56] References Cited

U.S. PATENT DOCUMENTS

| | | | |
|---|---|---|---|
| 2,819,774 | 1/1958 | Schmidt et al. | 73/863.23 X |
| 2,982,131 | 5/1961 | Rosinski | 73/863.03 |
| 3,261,199 | 7/1966 | Raynor | 73/863.03 |
| 3,603,155 | 9/1971 | Morris et al. | 73/863.02 X |
| 3,784,902 | 1/1974 | Huber | 73/863.03 X |
| 3,841,145 | 10/1974 | Boubel | 73/863.03 |
| 3,842,678 | 10/1974 | De Baun et al. | 73/863.03 |
| 3,866,475 | 2/1975 | Thompson et al. | 73/863.03 |
| 3,921,458 | 11/1975 | Logan | 73/863.58 |
| 3,930,414 | 1/1976 | Russell | 73/863.03 |
| 3,965,748 | 6/1976 | Boubel et al. | 73/863.03 |
| 4,091,835 | 5/1978 | Frampton | 73/863.03 X |
| 4,159,635 | 7/1979 | Sehmel | 73/863.03 X |
| 4,506,553 | 3/1985 | Bruce et al. | 73/861.65 |
| 4,566,342 | 1/1986 | Kurz | 73/863.03 |
| 4,649,760 | 3/1987 | Wedding | 73/863.23 |
| 5,010,771 | 4/1991 | Bruce | 73/861.18 |

FOREIGN PATENT DOCUMENTS

| | | | |
|---|---|---|---|
| 400834 | 10/1973 | U.S.S.R. | 73/863.25 |
| 1154582 | 5/1985 | U.S.S.R. | 73/863.02 |
| 1163192 | 6/1985 | U.S.S.R. | 73/863.23 |

OTHER PUBLICATIONS

"Aerosol Transport Through a Porous Sampling Probe with Transpiration Air Flow"; *Journal of Colloid and Interface Science*, vol. 56, No. 1, Jul. 1976, pp. 42–52; by Madhaw B. Ranade et al.

*Primary Examiner*—Tom Noland
*Attorney, Agent, or Firm*—Saul Elbaum; Guy M. Miller; Paul S. Clohan

[57] ABSTRACT

An automatic isokinetic sampling device for measuring aerosols in a fluid flow has a vacuum or suction pressure device attached to the end of a tubular collector which is placed in the path of the fluid flow. A differential air flow sensor senses and determines the difference in velocity between the fluid flow outside the tubular collector and that portion of the fluid flow received by the tubular collector. A filter for collecting a sample the aerosols in the fluid flow is placed along the straight downwind path of the fluid flow and within the tubular collector. As the fluid flow velocity changes the flow inside the tubular collector is equalized to the flow outside the tubular collector providing isokinetic sampling of the aerosols.

5 Claims, 2 Drawing Sheets

AUTOMATIC ISOKINETIC AEROSOL SAMPLING SYSTEM

RIGHTS OF THE GOVERNMENT

The invention described herein may be manufactured, used and licensed by or for the United States Government for Governmental Purposes without payment to me of any thereon.

BACKGROUND OF THE INVENTION

This invention relates to apparatus for sampling aerosols in a gas flow and, more particularly, to apparatus adapted for isokinetic sampling of a gas flow.

It is difficult to sample a fluid without disturbing the condition or composition of a fluid flow system. Any disturbance may have adverse effects on the system composition and prevent the extraction of a truly representative sample of the fluid. In particular, accurate sampling of aerosols, which winds greater than 2m/sec, etc.), is particularly difficult. aerosol may be defined as a group of solid particles or liquid particles suspended in a gaseous medium. The size range of these particles is generally between 10 nanometers and 100,000 nanometers in diameter. In an aerosol, the large particles account for most of the mass or weight of an aerosol. From observation, it appears that the particle sizes between 100 nanometers and 1,000 nanometers cause the greatest health impairment and also cause the greatest decrease of visibility in the atmosphere.

Sampling apparatus heretofore available for measuring particulate matter under isokinetic flow conditions have required considerable manual adjustment during use. An apparatus of this type is shown in Boubel, U.S. Pat. No. 3,841,145. This sampler comprises a generally cylindrical tube and includes an inlet nozzle disposed at the forward end of the tube and adapted for insertion into a conduit through which a gas is flowing. A pitot tube is attached to the nozzle and is adapted for insertion into the conduit with the nozzle for measuring the velocity of gas flowing through the conduit. A filter is disposed in the tube downstream of the nozzle for collecting particulate matter. The filter is disposed in a housing which comprises upstream and downstream sections removably connected together to facilitate rinsing of the sampler upstream of the filter as is necessary fully to account for particulate matter removed from the flow.

Another sampling apparatus is shown in Logan, U.S. Pat. No. 3,921,458. This system consists of a circularly arcuate tube having a first end to be disposed outside a conduit through which fluid travels along a flow path, and a second end disposed inside the conduit at or near its center in a plane aligned to the flow path of the fluid and substantially parallel thereto. The second end of the tube faces the path of fluid flow for accurate sampling of the fluid with minimal disturbance to flow. The first end of the tube is connectable to sampling means capable of withdrawing fluid from the conduit at the same linear velocity of the fluid flowing through the conduit. A supporting sleeve is attached to the conduit by an external weld joint where the tube enters the conduit and acts in cooperation with a combined seal to seal the probe against leakage, control the extension of the probe into the conduit as well as align it with the axial path of flow of fluid through the conduit for accurate sampling of the fluid composition.

A further sampling apparatus is shown in Boubel et al., U.S. Pat. No. 3,965,748. In this system, a sampler for collecting particulate samplings in gaseous emissions includes means for automatically matching the volume rate of flow through the sampler to the flow in a stack. Pressure drops and temperatures in the stack and in the sampler are continuously detected and applied to calculating circuitry which controls a valve in the sampler for maintaining isokinetic flow conditions. A filter is removably disposed in the sampler to collect particulate material from the gaseous emission during the isokinetic flow which is obtained. Flow and flow rate are also detected and displayed.

OBJECTS AND SUMMARY OF THE INVENTION

It is the principal object of the present invention to provide an improved automatic isokinetic sampling apparatus that will accurately sample aerosol densities from a moving airstream.

For accuracy of the mass determination for minimal sampling times so as to best describe aerosol clouds, it is important to precisely match the air flow rate, over a wide range of air speeds, at high volume sampling rates. There is no available system that accomplishes this. Others who claim to have matched air flow rates simply match average wind speeds. Research indicates that this is not nearly accurate enough to measure, for example, dust clouds in all wind conditions. The electro-mechanical unit described below will match the wind speed down to the order of 0.1 m/sec and up to at least 15 m/sec. Both mechanical and electro-mechanical embodiments are described. In both cases, the purpose is to ensure that air flow lines upwind of the sampler are not disturbed by the sampler because, when this occurs, aerosol particles separate from the air flow thereby distorting the apparent density measured by altering the ratio of the aerosol mass collected on the filter to the volume of air sampled.

In either embodiment, it is important to create an air speed at the entrance of the sampler that is equal to the value that would have appeared there if the sampler were absent. This requires attention to the edges of the sampling aperture, as well as to the central portion, but the edge design is easily handled using well known aerodynamic considerations.

The mechanical unit uses a shutter (butterfly) valve behind the filter in the sampler, and the electro-mechanical unit uses a very sensitive, fast response differential wind sensor in conjunction with an electronic servo, to equalize the air flow rates at and adjacant to the entrance of the sampler. In the electro-mechanical unit, the electronic servo unit adjusts the motor speed to bring the air speed difference to zero in a very short time interval, usually from 0.1 to 1.0 seconds.

DETAILED DESCRIPTION OF THE PREFERRED EMBODIMENTS

Figure 1:
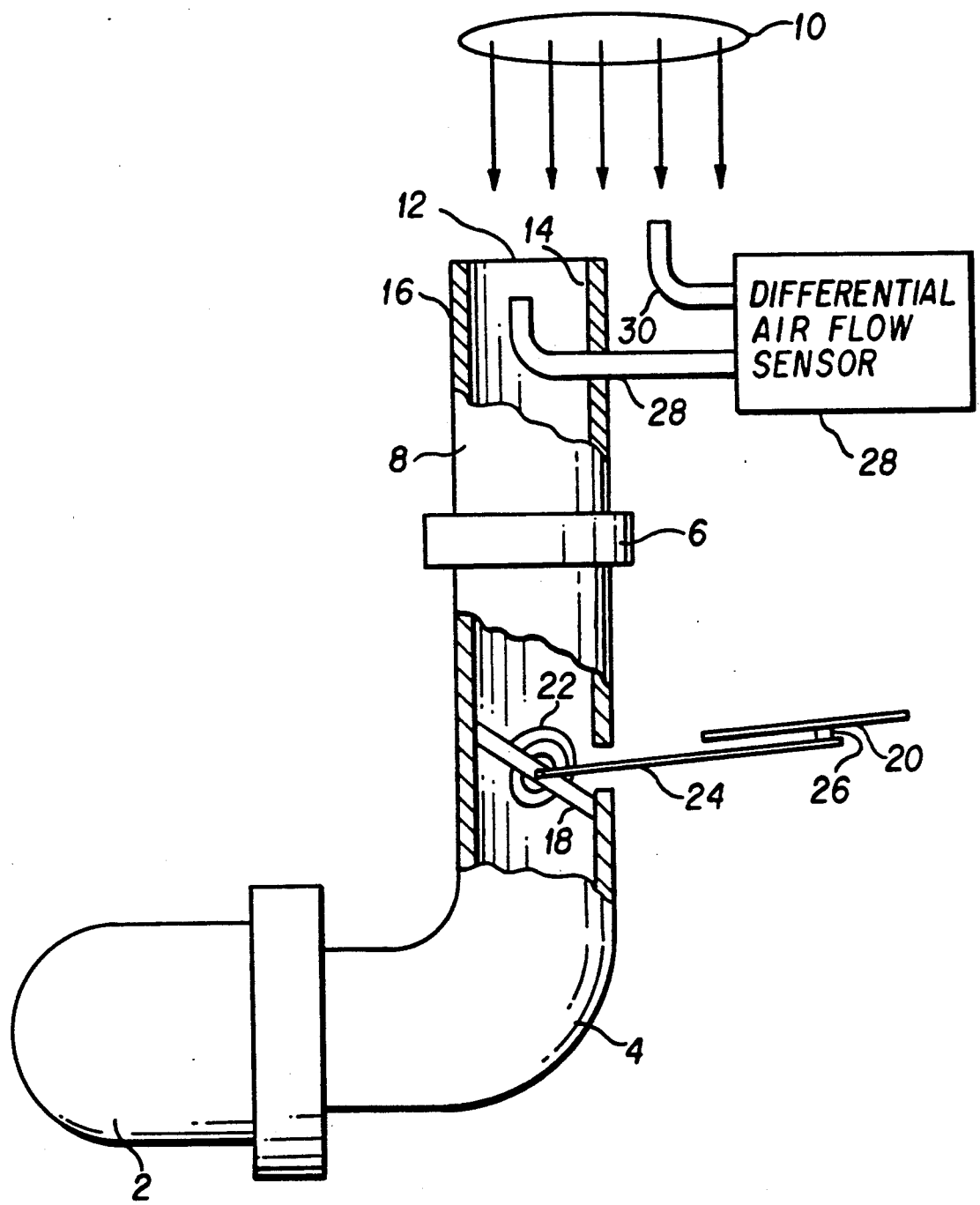
FIG. 1 is a depiction of a mechanical embodiment of the present invention.

Referring now to FIG. a mechanical Isokinetic Aerosol Sampling System according to the present invention is shown. A CADILLAC vacuum motor 2 is connected to a lower sampling tube 4. At the upper end of lower sampling tube 4 is attached, in the normal manner, a GELMAN filter holder 6. To collect samples of incoming fluid stream 10, an upper cylindrical collection tube 8 is fitted to the GELMAN filter holder 6. Those skilled in the art will recognize that the above components are well known and require no further detailed description.

To ensure accurate aerosol dosimetry, the air flow lines upwind of the sampling system must not be disturbed by the sampler. If these lines are disturbed, the aerosol particles separate from the air flow thereby distorting the apparent density measured by altering the ratio of the aerosol mass collected on filter 6 to the volume of fluid 10 sampled. Therefore, it is necessary to create an air flow velocity at entrance 12 of the sampler that is equal to the velocity of flow that would have appeared there if the sampler were absent. This process requires attention to edges 14 and 16 of entrance 12, as well as to the central portion of upper sampling tube 8, but the edge design is easily handled using well known aerodynamic considerations.

The mechanical Isokinetic Aerosol Sampling System shown in FIG. 1 uses a shutter (i.e. butterfly) valve 18 behind filter holder 6 to equalize the air flow rates at and adjacent to entrance 12 of the sampler. Equalization of the air flow rates is accomplished by the shutter valve 18 in combination with vane 20. Shutter valve 18, mounted within lower sampling tube 4 on bearings in any well known method, has attached a return spring 22 and an external arm 24 with vane 20 slidably attached at attachment point 26, so that the distance from the center of vane 20 to the pivot point of shutter valve 18 can be varied. The fluid stream 10 (e.g. air, wind, smoke, etc.) is drawn through entrance 12 of upper sampling tube 8, through filter 6, and then past shutter valve 18 by the high flow-rate vacuum motor 2. Because vane 20 and shutter valve 18 are rigidly attached by arm 24, when the fluid stream 10 impinges on vane 20, shutter valve 18 will open and allow vacuum motor 2 to produce a flow rate through upper sampling tube 8 and lower sampling tube 4 that is equal to the flow rate of fluid stream 10 outside the sampler. In actual use, vane 20 is adjusted towards or away from the pivot point of shutter valve 18 in order to fine tune the operation of shutter valve 18. As fluid stream 10 flow rate changes, vane 20 will compensate for an increase in wind speed by opening shutter valve 18 and allowing vacuum motor 2 to draw more fluid through the sampler, and return spring 22 will compensate for a decrease in wind speed by closing shutter valve 18 thereby reducing the amount of fluid through the sampler.

In order to set the sampler up for equal flow speeds over as wide a fluid speed range as possible and to monitor the sampler during use to ensure that the unit is operating properly, a differential air flow sensor 28 is incorporated in the sampler system. Briefly, the differential air flow sensor 28 operates as follows: a gas flow alternator cyclically connects a microphone to the dynamic flow pressure, provided by dynamic air flow data tube 28, and then to the reference flow pressure outside the sampler, provided by reference air data tube 30. The microphone converts these pressures to a resultant alternating differential signal providing a first input to a phase-locked amplifier. A second amplifier input is derived from an optical pickup mounted within the alternator housing. A readout connected in the circuit with the amplifier indicates the resultant differential flow pressure. A detailed description of a suitable differential air flow sensor is provided in U.S. Pat. No. 4,506,553 which is hereby incorporated by reference. Thus when the pressure difference between tube 28 and tube 30 is zero, the flow rate through the sampler matches the flow rate of the incoming fluid, and the unit is balanced.

Figure 2:
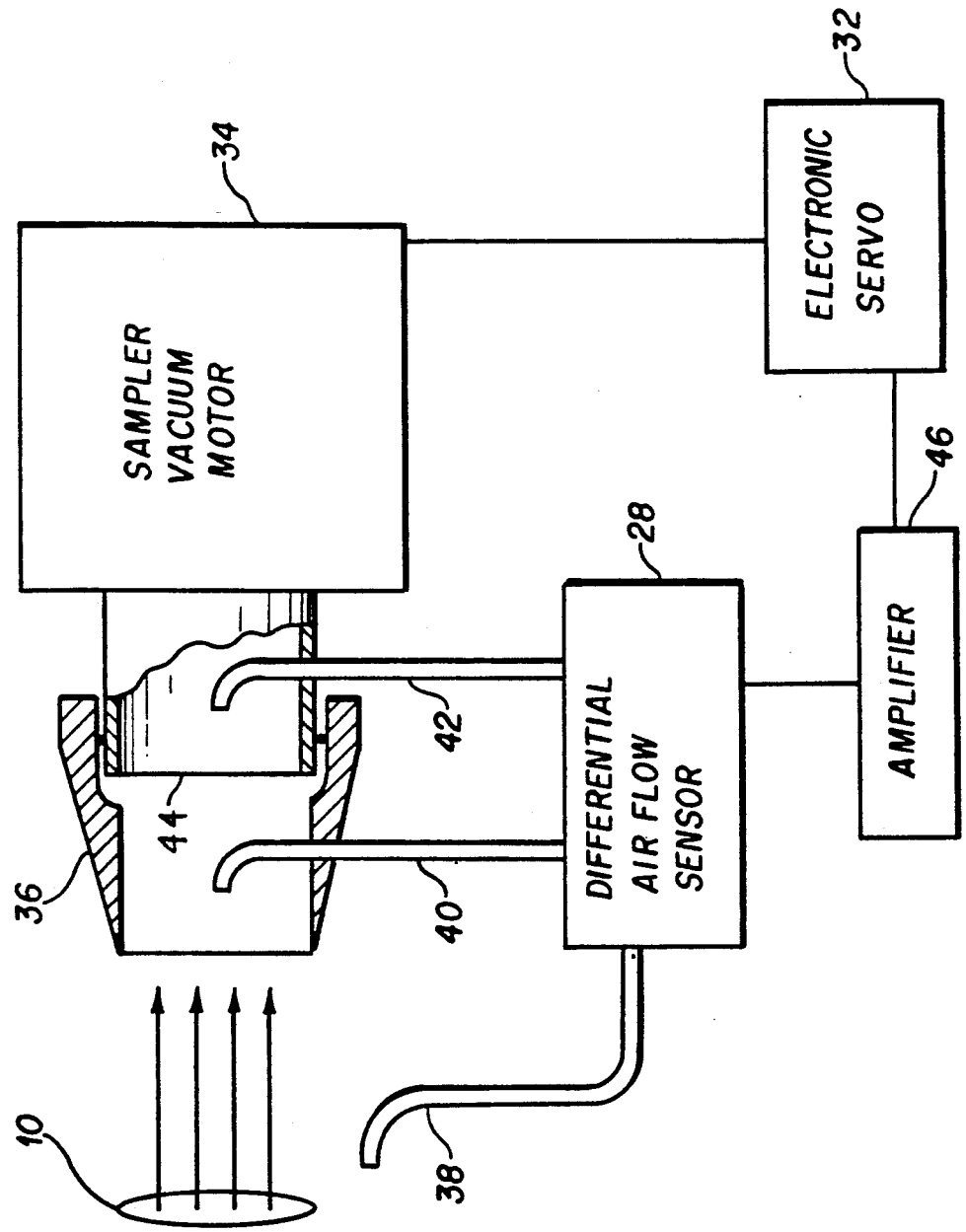
FIG. 2 is a depiction of an electro-mechanical embodiment of the present invention.

An alternate embodiment of the present invention is shown in FIG. 2, which is an electro-mechanical version of the sampler. This unit can sense and respond very quickly due to the rapid response of the differential air flow sensor 28 used in conjunction with an electronic servo 32. The differential air flow sensor is the same sensor as described above in the mechanical sampler. The limit of response for the electro-mechanical unit is the inertial lag of the motor rotor (armature) of sampler vacuum motor 34. This inertial lag can be made very small by over-driving motor 34 when rapid changes are required. The distinct advantage of the electronic servo 32 is that the motor driver can be tailored to suit the requirements of the motor and the required response. These techniques are well known in the art. In this system, very small scale turbulence (which involves rapid changes in direction as well) are not matched precisely; however, these factors are minute in magnitude and importance for aerosol sampling.

The sampler vacuum motor 34 is from a standard commercial sampler that is not normally wind-matched (commonly known as a high volume sampler) which, like the mechanical embodiment, allows collection of particles at a relatively high rate which is necessary for the analyses of the acquired particulate matter. In this embodiment, the effective sampling diameter is about 4 inches for sampling head 36. Differential air flow sensor 28 receives reference and dynamic inputs from probes 38 and 40 or 42 respectively. The difference between input probes 40 and 42 is not critical to the function of differential air flow sensor 28, and the user may select either input depending upon his particular application. Probe 42 will deliver the pressure behind filter 44 and probe 40 will deliver a slight higher pressure and thus would most likely be the one chosen. In either case, the output of differential air flow sensor 28 is amplified by amplifier 46 and used as the input to electronic servo 32. Electronic Servo 32 then raises or lowers the voltage to vacuum motor 34, thus balancing the flow rate through the sampler to that of the oncoming fluid stream 10. Filter 44, on which the aerosol is collected, is preferably either a plastic (polycarbonate) or fiberglass mat, or may be selected otherwise as is well known in the art. The entire electro-mechanical sampler may then be vane mounted or oriented into the wind, for experiments with wind oriented grids.

To those skilled in the art, many modifications and variations of the present invention are possible in light of the above teachings. It is therefore to be understood that the present invention can be practiced otherwise than as specifically described herein and still will be within the spirit and scope of the appended claims.

I claim:

1. An automatic isokinetic sampling device for measuring aerosols in a fluid flow comprising:
   tubular means for insertion in said fluid flow for receiving a portion of said fluid flow without substantially disturbing the fluid flow upwind of said tubular means,
   filter means disposed along the straight downwind path of said fluid flow and within said tubular means for collecting a sample of said aerosols from said portion of said fluid flow, suction pressure applying means attached to said tubular means for moving said portion of said fluid flow through said tubular means;

means responsive to said fluid flow for adjusting the velocity of said portion of said fluid flow moving through said tubular means;

a differential air flow sensor having a reference air flow data tube disposed within said fluid flow and a dynamic air flow data tube disposed within said portion of said fluid flow for determining the difference in velocity between said fluid flow and said portion of said fluid flow moving through said tubular means.

2. The device of claim 1 wherein said means responsive to said fluid flow for adjusting the velocity of said portion of said fluid flow moving through said tubular means comprises a shutter valve disposed within said tubular means, said shutter valve having an arm rigidly attached thereto with said arm having a vane slideably attached thereto, said vane responsive to said fluid flow so as to open said shutter valve as said fluid flow velocity increases, said shutter valve also having a spring attached thereto so as to close said shutter valve as said fluid flow velocity decreases.

3. The device of claim 1 wherein said means responsive to said fluid flow for adjusting the velocity of said portion of said fluid flow moving through said tubular means comprises an amplifier connected to the output of said differential air flow sensor and an electronic servo having an input from said amplifier and an output to said suction pressure applying means thereby adjusting the velocity of said portion of said fluid flow moving through said tubular means when the output of said differential air flow sensor indicates a difference in velocity between said fluid flow and said portion of said fluid flow.

4. An automatic isokinetic sampling apparatus for measuring aerosols in a fluid flow comprising:

a vacuum motor;

a lower sampling tube connected at one end to said vacuum motor;

a butterfly valve pivotally disposed in said lower sampling tube, said butterfly valve having an arm attached thereon, said arm extending outward from said lower sampling tube, and said arm having a vane slideably attached near an end of said arm opposite of said butterfly valve, said vane being disposed in said fluid flow and responsive thereto;

said butterfly valve having a coiled spring attached thereon so as to act on said butterfly valve in a manner opposite to that of said vane;

a filter holder having a filter disposed thereon attached at an end of said lower sampling tube opposite to that connected to said vacuum motor;

an upper sampling tube for receiving a portion of said fluid flow attached to said filter holder having an open end facing said fluid flow, said upper sampling tube having a dynamic air flow data tube disposed therein, said dynamic flow data tube open to said portion of said fluid flow moving within said upper sampling tube;

a reference air data tube located external to said upper sampling tube;

a differential air flow sensor having one input from said dynamic air flow data tube and a second input from said reference air data tube thereby providing a determination of the difference in velocity of said portion of said fluid flow moving within said upper sampling tube and said fluid flow external to said upper sampling tube.

5. An automatic isokinetic sampling apparatus for measuring aerosols in a fluid flow comprising:

a vacuum motor;

a filter holder having a filter disposed thereon attached to said vacuum motor;

a sampling head for receiving a portion of said fluid flow attached to said filter holder, said sampling head open to said fluid flow, said sampling head having a dynamic air flow data tube disposed therein, said dynamic air flow data tube open to said portion of said fluid flow moving within said sampling head;

a reference air data tube located external to said sampling head;

a differential air flow sensor having one input from said dynamic air flow data tube and a second input from said reference air data tube thereby providing a signal consisting of the difference in velocity between said portion of said fluid flow moving within said sampling head and said fluid flow that is external to said sampling head;

an amplifier connected to said differential air flow sensor for amplifying said signal;

an electronic servo connected to said amplifier responsive to said amplified signal, said electronic servo also connected to said vacuum motor thereby adjusting the speed of said vacuum motor in proportion to said signal so as to control the velocity of said portion of said fluid flow moving through said sampling head.

* * * * *